US012059277B2

(12) United States Patent
Lyu

(10) Patent No.: US 12,059,277 B2
(45) Date of Patent: Aug. 13, 2024

(54) SYSTEMS AND METHODS FOR POSITRON EMISSION TOMOGRAPHY IMAGING

(71) Applicant: SHANGHAI UNITED IMAGING HEALTHCARE CO., LTD., Shanghai (CN)

(72) Inventor: Xinyu Lyu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 319 days.

(21) Appl. No.: 17/596,104

(22) PCT Filed: Jun. 4, 2020

(86) PCT No.: PCT/CN2020/094466
§ 371 (c)(1),
(2) Date: Dec. 3, 2021

(87) PCT Pub. No.: WO2020/244603
PCT Pub. Date: Dec. 10, 2020

(65) Prior Publication Data
US 2022/0304633 A1 Sep. 29, 2022

(30) Foreign Application Priority Data
Jun. 5, 2019 (CN) .......................... 201910485777.4

(51) Int. Cl.
*A61B 6/03* (2006.01)
*A61B 6/00* (2024.01)
*A61B 6/42* (2024.01)

(52) U.S. Cl.
CPC ............ *A61B 6/037* (2013.01); *A61B 6/4266* (2013.01); *A61B 6/5205* (2013.01); *A61B 6/563* (2013.01)

(58) Field of Classification Search
CPC ..... A61B 6/037; A61B 6/4266; A61B 6/5205; A61B 6/563
See application file for complete search history.

(56) References Cited

U.S. PATENT DOCUMENTS

| 5,841,140 A | * | 11/1998 | Mc Croskey | ........ A61B 6/4258 |
| | | | | 250/363.04 |
| 6,858,847 B1 | * | 2/2005 | Macciocchi | .......... G01T 1/2985 |
| | | | | 250/363.03 |

(Continued)

FOREIGN PATENT DOCUMENTS

| CN | 101365963 A | 2/2009 |
| CN | 103890611 A | 6/2014 |

(Continued)

OTHER PUBLICATIONS

International Search Report in PCT/CN2020/094466 mailed on Sep. 1, 2020, 5 pages.

(Continued)

*Primary Examiner* — Blake C Riddick
(74) *Attorney, Agent, or Firm* — METIS IP LLC

(57) ABSTRACT

A method for positron emission tomography (PET) imaging may include obtaining photon information of photons that are emitted from an object and detected by detector units of a detector of a PET scanner. The method may also include obtaining, based on the photon information and lines of response (LORs), more than one coincidence window width value of the PET scanner. The method may also include determining coincidence events of the photons based on the more than one coincidence window width value.

20 Claims, 8 Drawing Sheets

(56) References Cited

U.S. PATENT DOCUMENTS

| | | | |
|---|---|---|---|
| 7,402,807 B2 | 7/2008 | Conti | |
| 7,985,958 B2 | 7/2011 | Nakasugi et al. | |
| 9,958,559 B1* | 5/2018 | Feng | G01T 1/2985 |
| 10,484,594 B2 | 11/2019 | Yamamoto | |
| 2005/0205791 A1* | 9/2005 | Bryman | G01T 1/172 |
| | | | 250/363.03 |
| 2006/0138332 A1* | 6/2006 | Bryman | G01T 1/172 |
| | | | 250/363.03 |
| 2006/0239398 A1* | 10/2006 | McCroskey | A61B 5/415 |
| | | | 600/407 |
| 2006/0249682 A1* | 11/2006 | Hogg | G01T 1/2985 |
| | | | 250/363.03 |
| 2007/0040122 A1* | 2/2007 | Manjeshwar | G01T 1/2985 |
| | | | 250/363.03 |
| 2007/0080295 A1* | 4/2007 | Hamill | A61B 6/037 |
| | | | 250/363.03 |
| 2007/0085013 A1* | 4/2007 | Watson | G01T 1/2985 |
| | | | 250/363.07 |
| 2007/0106154 A1 | 5/2007 | Conti | |
| 2007/0147589 A1* | 6/2007 | Thielemans | G06T 11/005 |
| | | | 378/207 |
| 2008/0099686 A1* | 5/2008 | Defrise | G01T 1/2985 |
| | | | 250/363.04 |
| 2008/0296505 A1* | 12/2008 | Cooke | A61B 6/037 |
| | | | 250/363.04 |
| 2009/0072154 A1* | 3/2009 | Watson | A61B 6/037 |
| | | | 250/363.03 |
| 2009/0074152 A1* | 3/2009 | Chen | G01T 1/169 |
| | | | 378/207 |
| 2009/0257633 A1* | 10/2009 | Cook | G16H 30/40 |
| | | | 382/131 |
| 2010/0230602 A1* | 9/2010 | Scheins | G01T 1/2985 |
| | | | 250/362 |
| 2011/0127413 A1* | 6/2011 | Casey | G01T 1/2985 |
| | | | 250/363.04 |
| 2012/0290519 A1* | 11/2012 | Fontaine | G01T 1/2985 |
| | | | 250/252.1 |
| 2013/0240721 A1* | 9/2013 | Laurence | G01T 1/164 |
| | | | 250/252.1 |
| 2013/0261440 A1* | 10/2013 | Georgi | A61B 6/4417 |
| | | | 600/436 |
| 2013/0304386 A1* | 11/2013 | Niu | G16B 5/00 |
| | | | 702/19 |
| 2013/0311142 A1 | 11/2013 | Wang et al. | |
| 2014/0095106 A1* | 4/2014 | Wang | A61B 6/037 |
| | | | 702/157 |
| 2014/0126793 A1* | 5/2014 | Ahn | G06T 11/006 |
| | | | 382/131 |
| 2014/0217294 A1* | 8/2014 | Rothfuss | G01T 1/1617 |
| | | | 250/362 |
| 2014/0257096 A1* | 9/2014 | Prevrhal | A61B 6/481 |
| | | | 600/431 |
| 2014/0374607 A1 | 12/2014 | Pistorius et al. | |
| 2015/0119694 A1* | 4/2015 | Mihlin | G06T 11/006 |
| | | | 600/411 |
| 2015/0241576 A1* | 8/2015 | Rothfuss | G01T 1/2985 |
| | | | 250/362 |
| 2016/0131774 A1* | 5/2016 | Lage | A61B 6/5217 |
| | | | 600/425 |
| 2016/0135768 A1 | 5/2016 | Wollenweber et al. | |
| 2016/0282486 A1* | 9/2016 | Balakrishnan | A61B 5/0033 |
| 2016/0306054 A1 | 10/2016 | Prevrhal et al. | |
| 2017/0032545 A1* | 2/2017 | Mihlin | A61B 6/037 |
| 2017/0046857 A1* | 2/2017 | Ye | G06T 3/40 |
| 2017/0082759 A1* | 3/2017 | Lyu | G01T 7/005 |
| 2017/0371046 A1* | 12/2017 | Laurence | G01T 1/249 |
| 2018/0114346 A1* | 4/2018 | Sun | G06T 11/005 |
| 2018/0144513 A1* | 5/2018 | Liu | G06T 7/0012 |
| 2018/0203141 A1* | 7/2018 | Chang | G06T 11/005 |
| 2018/0356536 A1* | 12/2018 | Glowacz | G01T 1/2985 |
| 2019/0287275 A1* | 9/2019 | Zhu | G06T 7/0012 |
| 2019/0371017 A1* | 12/2019 | Zhu | G06T 11/005 |
| 2020/0286266 A1* | 9/2020 | Song | G01T 1/2985 |
| 2020/0363542 A1* | 11/2020 | Song | G01T 1/171 |
| 2021/0030387 A1* | 2/2021 | Andreyev | A61B 6/5282 |
| 2021/0366165 A1* | 11/2021 | Song | G06T 11/005 |
| 2022/0057344 A1* | 2/2022 | Connell | G01T 1/2985 |

FOREIGN PATENT DOCUMENTS

| | | |
|---|---|---|
| CN | 104644204 A | 5/2015 |
| CN | 105354427 A | 2/2016 |
| CN | 110215227 A | 9/2019 |
| JP | 2013113714 A | 6/2013 |

OTHER PUBLICATIONS

Written Opinion in PCT/CN2020/094466 mailed on Sep. 1, 2020, 6 pages.

First Office Action in Chinese Application No. 201910485777.4 mailed on Dec. 3, 2020, 19 pages.

* cited by examiner

SYSTEMS AND METHODS FOR POSITRON EMISSION TOMOGRAPHY IMAGING

CROSS-REFERENCE TO RELATED APPLICATIONS

This application is a U.S. national stage under 35 U.S.C. § 371 of International Application No. PCT/CN2020/094466, filed on Jun. 4, 2020, which claims priority to Chinese Patent Application No. 201910485777.4, filed on Jun. 5, 2019, the entire contents of each of which are hereby incorporated by reference.

TECHNICAL FIELD

The present disclosure generally relates to positron emission tomography (PET), and more specifically relates to systems and methods for determining several coincidence time windows.

BACKGROUND

Positron Emission Tomography (PET) is a technology developed in nuclear medicine. It is non-invasive and able to provide high-quality images. To perform a PET scan on a patient using a PET scanner, a certain substance labeled with a positron radioactive element is first injected into the patient or animal. The radioactive element may decay in the body and emit positrons, which may have a certain kinetic energy, exist in an unstable state with a short lifetime. When colliding with tissue in the body, the positrons may run out of the kinetic energy and annihilate with negative electrons in the tissue, simultaneously produces two photons with the same energy of 511 keV. Photons have a strong penetrating power and can penetrate living organisms. The photons subsequently are detected by detectors of the PET scanner. Tomographic images are formed by collecting data from many angles around the patient, resulting in PET images. As a result, the electron and the positron annihilation position can be determined. A common structure of the detector of the PET scanner is a ring comprising of many crystals. A target object (e.g., a patient) may be located inside the ring. Two photons emitted from a same annihilation position in the body may penetrate the body along nearly opposite directions. The two photons may be detected by two units of the detector, respectively. A straight line connecting the two detector units is referred to as a line of response (LOR) corresponding to the two photons that is deemed to correspond to a coincidence event. The determination of coincidence events is the core principle and a basic function of PET imaging system.

Photons may travel nearly at the speed of light. The photons that are generated in a positron and an electron annihilation transmitting from the body may be detected at almost the same time. A tiny difference between the times when the two photons are detected may depend on the location of the annihilation position on the LOR. During a process for determining a coincidence event, when a first detector unit detects a first photon, a coincidence time window may be set for the other photon. The coincidence time window is a concept of a time range. If a second detector unit connected by the LOR corresponding to the first photon receives a second photon within the coincidence time window, the first and the second photons may be reference as from the same annihilation event, and a valid coincidence event is recorded. In the prior art, for a PET imaging system, a uniform coincidence time window is usually set for all LORs in a PET system according to the longest LOR of the PET system. However, for shorter LORs detected in the PET system, the uniform coincidence time window may be too large, which results in errors in determining the coincidence events and reduced imaging quality. Therefore, it is desirable to provide systems and/or methods for determining several coincidence time windows to improve the accuracy of determining coincidence events.

SUMMARY

According to a first aspect of the present disclosure, a system for positron emission tomography (PET) imaging may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain photon information of photons that are emitted from an object and detected by detector units of a detector of a PET scanner. The one or more processors may obtain, based on the photon information and lines of response (LORs), more than one coincidence window width value of the PET scanner. The one or more processors may determine coincidence events of the photons based on the more than one coincidence window width value.

In some embodiments, the obtaining, based on the photon information, the more than one coincidence window width value may include the following operations. The one or more processors may determine, based on the photon information, target LOR information of the target LORs. The one or more processors may obtain the more than one coincidence window width value based on the target LOR information of the target LORs.

In some embodiments, the target LOR information of each of the target LORs may include at least one of a first length of the target LOR, an incident angle corresponding to the target LOR, and location information of two of the detector units connected by the target LOR.

In some embodiments, the obtaining the more than one coincidence window width value corresponding to the target LORs based on the target LOR information may include the following operations. For each of the target LORs, the one or more processors may determine a second length of a segment of the target LOR in a field of view (FOV) of the PET scanner based on the target LOR information of the target LOR. The one or more processors may obtain the more than one coincidence window width value based on the second lengths.

In some embodiments, the obtaining the more than one coincidence window width value corresponding to the target LORs based on the target LOR information may include the following operations. The one or more processors may obtain a mapping relation between the more than one coincidence window width value and the target LOR information of the target LORs. The one or more processors may obtain the more than one coincidence window width value by consulting the mapping relation based on the target LOR information of the target LORs.

In some embodiments, the mapping relation may be provided by: for each candidate LOR connecting two of the detector units of the detector in the PET scanner, obtaining candidate LOR information of the candidate LOR; determining a third length of a segment of the candidate LOR in a field of view (FOV) of the PET scanner based on the candidate LOR information; determining a candidate window width value corresponding to the candidate LOR based on the third length; and generating the mapping relation based on the candidate window width value corresponding to each candidate LOR and the candidate LOR information, the candidate LORs including the target LORs.

In some embodiments, the candidate LOR information of the candidate LOR may include at least one of a fourth length of the candidate LOR, an incident angle corresponding to the candidate LOR, and location information of the two of the detector units connected by the candidate LOR.

In some embodiments, the fourth length of the candidate LOR may be determined based on the incident angle corresponding to the candidate LOR or the location information of the two of the detector units connected by the candidate LOR.

In some embodiments, the determining the third length of the segment of the candidate LOR in the FOV of the PET scanner based on the candidate LOR information may include the following operations. The one or more processors may determine the third length based on the fourth length of the candidate LOR, a diameter of a bore of the PET scanner, and a diameter of the FOV.

In some embodiments, the determining the third length of the segment of the candidate LOR in the FOV of the PET scanner based on the candidate LOR information may include the following operations. The one or more processors may determine the third length based on the incident angle corresponding to the candidate LOR.

In some embodiments, the candidate window width value corresponding to the candidate LOR may be determined based on the third length and a speed of light.

In some embodiments, the candidate window width value corresponding to the candidate LOR may be determined based further on a coincidence temporal resolution of the PET scanner.

In some embodiments, the one or more processors may generate an image of the object based on the determined coincidence events.

According to another aspect of the present disclosure, a method for positron emission tomography (PET) imaging may include one or more of the following operations. One or more processors may obtain photon information of photons that are emitted from an object and detected by detector units of a detector of a PET scanner. The one or more processors may obtain, based on the photon information and lines of response (LORs), more than one coincidence window width value of the PET scanner. The one or more processors may determine coincidence events of the photons based on the more than one coincidence window width value.

According to yet another aspect of the present disclosure, a system for positron emission tomography (PET) imaging may include an obtaining module configured to obtain photon information of photons that are emitted from an object and detected by detector units of a detector of a PET scanner. The system may also include a setting module configured to obtain, based on the photon information and lines of response (LORs), more than one coincidence window width value of the PET scanner. The system may also include an event determination module configured to determine coincidence events of the photons based on the more than one coincidence window width value.

According to yet another aspect of the present disclosure, a non-transitory computer readable medium may comprise at least one set of instructions for positron emission tomography (PET) imaging. The at least one set of instructions may be executed by one or more processors of a computing device. The one or more processors may obtain photon information of photons that are emitted from an object and detected by detector units of a detector of a PET scanner. The one or more processors may obtain, based on the photon information and lines of response (LORs), more than one coincidence window width value of the PET scanner. The one or more processors may determine coincidence events of the photons based on the more than one coincidence window width value.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 3:
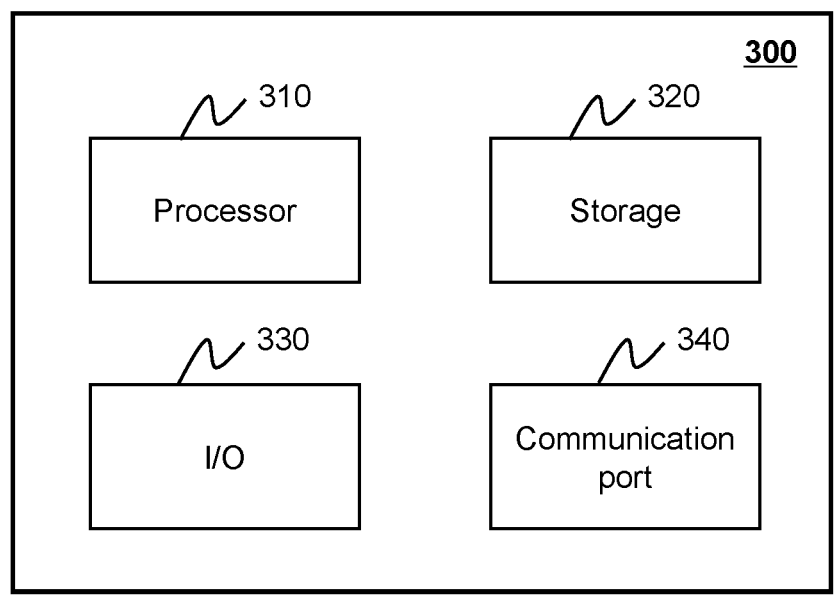
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

A coincidence event may be identified if the time difference between the detection of two gamma photons in a pair of oppositely disposed detector units is within a coincidence time window. The identified coincidence events may include true coincidence events, scattered coincidence events and random coincidence events. The true coincidence events may be those physically correlated time coincidences, i.e., two gamma photons emitted in the process of annihilation. The scattered events are in essence true coincidences, but one or both of the two annihilation photons has undergone a Compton scatter interaction. The random coincidence events may be those time coincidences that are not correlated, but randomly occur within the coincidence time window. For an LOR, the coincidence time window may be great enough to accept all true coincidence events occurring within the FOV. However, extending the coincidence time window may result in more random coincidence events.

In the prior art, for a PET imaging system, a uniform coincidence time window width value is usually set for all LORs in a PET system according to the longest LOR. However, for shorter LORs, the uniform coincidence time window width value may be too large, which results in more random coincidence events and reduced imaging quality, especially for three-dimensional (3D) acquisition by a PET system including a PET detector with a plurality of detector rings.

An aspect of the present disclosure relates to systems and methods for determining several different coincidence time windows width values. For an LOR, a coincidence time window with a window width value corresponding to the length of the LOR may be determined. A single event refers to the generation of a photon (e.g., a gamma photon). Compared to a uniform coincidence time window width value for all LORs, such LOR-dependent coincidence time window width values may be used to identify, from a large amount of single events, candidate single events more precisely, and accordingly reduce erroneously determined LORs and/or reduce the amount of single events to be processed in the coincident event determination, which in turn may improve the accuracy and/or efficiency in determining coincidence events and the image quality of the PET system. Moreover, the coincidence time window width value for an LOR may be determined without prior reconstruction of one or more images obtained by scanning a region of interest (ROI) of an object, further improving the efficiency of the imaging process.

The following description is provided to help better understanding systems and/or methods for determining a coincidence time window in PET imaging. This is not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

In the present disclosure, the terms "time window," "coincidence window," and "coincidence time window" may be used interchangeably. The terms "window width," "time window width," "coincidence window width," "window width value," "time window width value," "coincidence time window width," "coincidence time window width value," and "coincidence window width value" may be used interchangeably to refer to a value of a duration of a coincidence time window.

Figure 1:
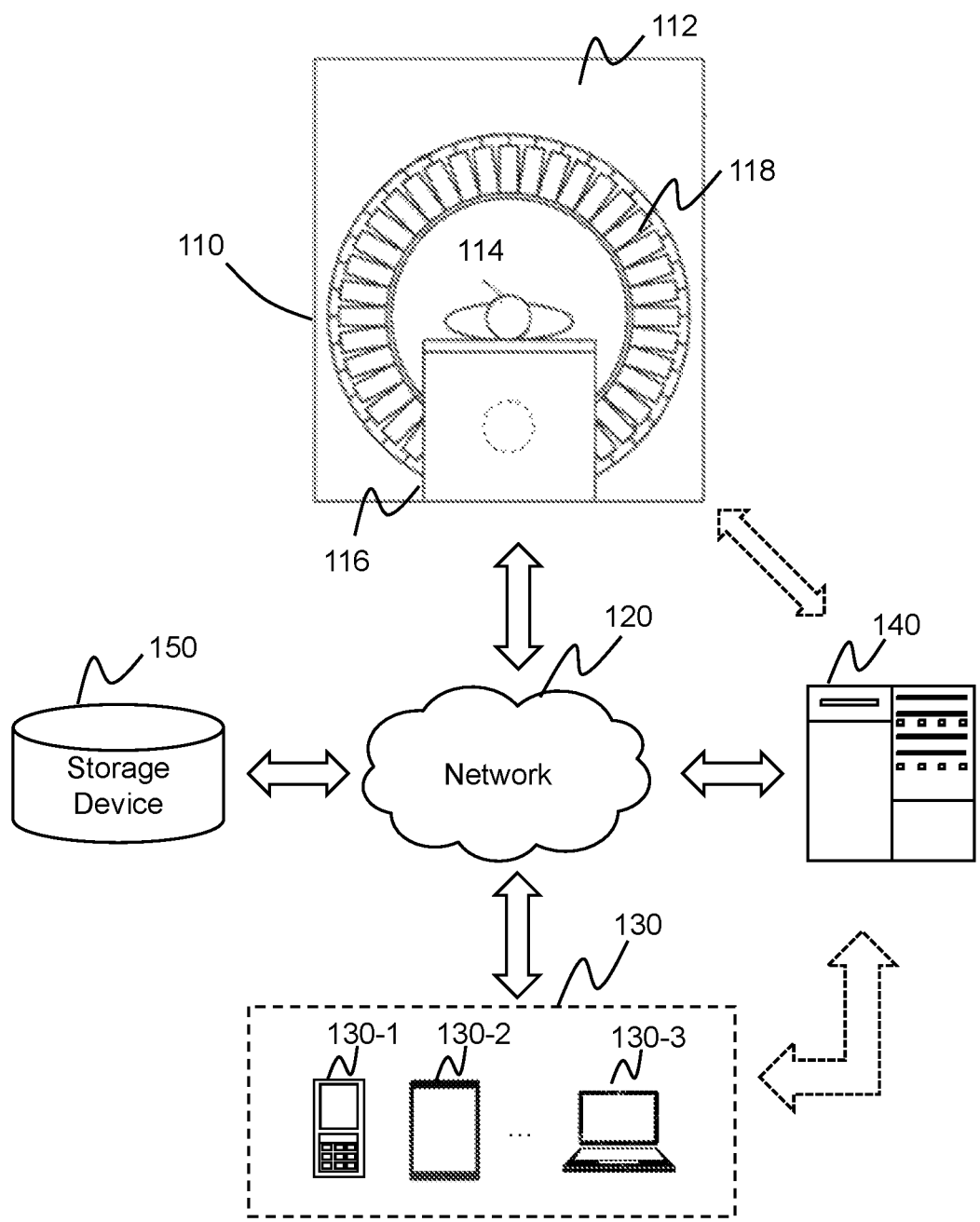
FIG. 1 is a schematic diagram illustrating an exemplary positron emission tomography (PET) system according to some embodiments of the present disclosure.

FIG. 1 is a schematic diagram illustrating an exemplary positron emission tomography (PET) system according to some embodiments of the present disclosure. PET imaging is based on coincidence events corresponding to detected photons arising from positron-electron annihilation.

The PET system 100 may include a PET scanner 110, a network 120, a terminal 130, a processing device 140, and a storage device 150. The components in the PET system 100 may be connected in one or more of various manners. Merely by way of example, the PET scanner 110 may be connected to the processing device 140 through the network 120. As another example, the PET scanner 110 may be connected to the processing device 140 directly (shown as the bi-directional arrow in dotted line linking the PET scanner 110 and the processing device 140). As another example, the processing device 140 may be connected to the storage device 150 through the network 120 or directly. As a further example, the processing device 140 may be connected to a terminal device (e.g., 130-1, 130-2, 130-3, etc.) through the network 120. As still a further example, the processing device 140 may be connected to a terminal device (e.g., 130-1, 130-2, 130-3, etc.) directly (shown as the bi-directional arrow in dotted line linking the terminal 130 and the processing device 140).

The PET scanner 110 may include a gantry 112, a table 116, and a detector 118. An object 114 injected with a substance (e.g., generally necessary for the metabolism of biological life, such as glucose, protein, nucleic acids, fatty acids, etc.) labeled with a tracer for the imaging purposes may be placed on the table 116. The detector 118 may be mounted on the gantry 112. The gantry 112 may form a detection tunnel (not shown in FIG. 1).

The tracer refers to a radioactive substance (e.g., radionuclides such as 18F, 11C, etc.) that decays and emits positrons. The object 114 may be biological or non-biological. Merely by way of example, the object 114 may include a patient, a man-made object, etc. As another example, the object 114 may include a specific portion, organ, and/or tissue of the patient. For example, the object 114 may include the head, the brain, the neck, the body, a shoulder, an arm, the thorax, the heart, the stomach, a blood vessel, a soft tissue, a knee, a foot, or the like, of a patient, or any combination thereof.

Figure 2:
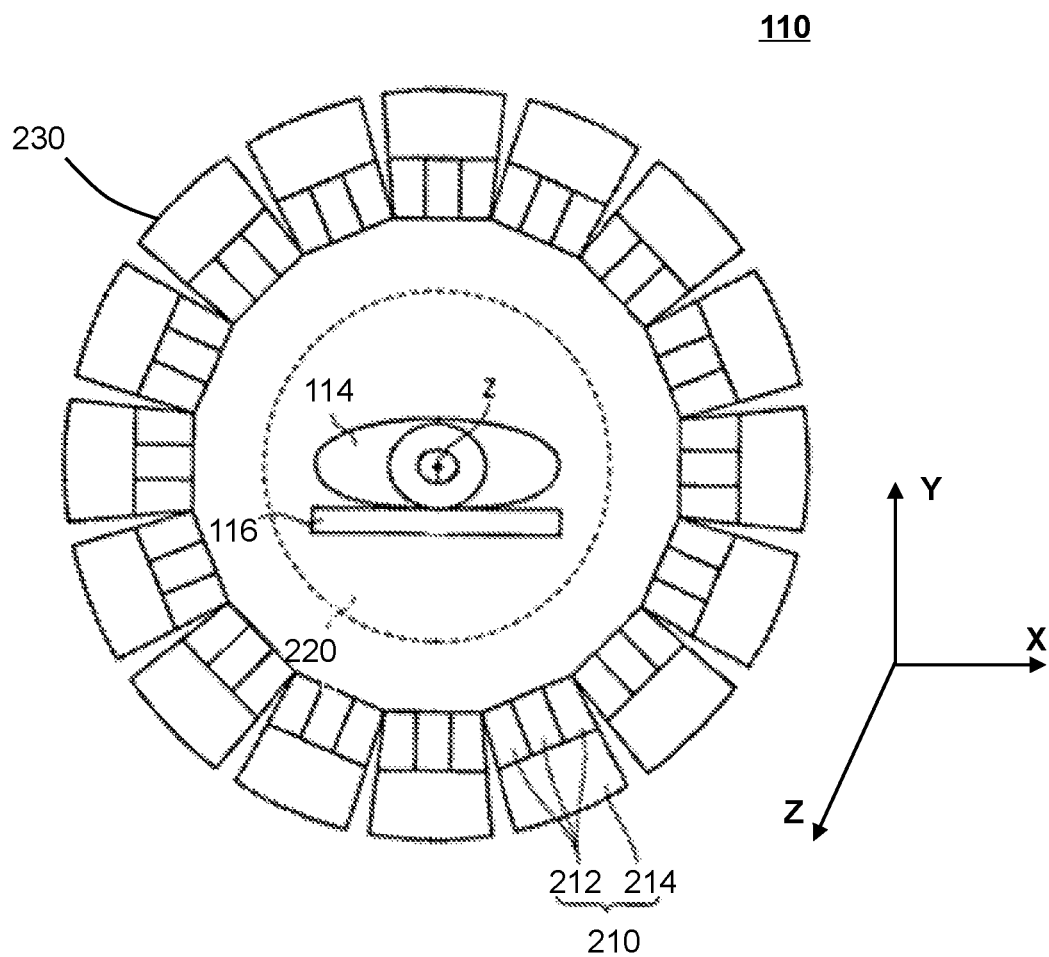
FIG. 2 is a cross section of an exemplary PET scanner according to some embodiments of the present disclosure.

In the present disclosure, the X axis, the Y axis, and the Z axis shown in FIG. 2 may form an orthogonal coordinate system. The X axis and the Z axis shown in FIG. 2 may be horizontal, and the Y axis may be vertical. As illustrated, the positive X direction along the X axis may be from the left side to the right side of the PET scanner 110 seen from the direction facing the front of the PET scanner 110; the positive Y direction along the Y axis shown in FIG. 2 may be from the lower part to the upper part of the PET scanner 110; the positive Z direction along the Z axis shown in FIG. 2 may refer to a direction in which the object is moved out of the scanning channel (or referred to as the bore) of the PET scanner 110.

As shown in FIG. 2, the detector 118 may include a plurality of detector rings (e.g., a detector ring 230) arranged along the Z direction (perpendicular to the paper as shown in FIG. 2). The plurality of detector rings may be located around the detection tunnel. A detector ring may include a plurality of detector units (e.g., a detector unit 210) arranged along the circumference of the detector ring.

The detector 118 may form a bore to accommodate the table 116. There may be a field of view (FOV) 220 in the bore. During a scan process, the object 114 along with the table 116 may be moved into the bore to position a region of interest (ROI) of the object 114 in the FOV 220.

As shown in FIG. 2, a detector unit 210 may include a scintillator 212 and a photodetector 214. The photodetector 214 may be operably coupled to the scintillator 212. In some embodiments, the scintillator 212 may include an array of scintillation crystals.

In some embodiments, positrons emitted from the radiation may travel through the object 114 until they encounter electrons. When a positron and an electron meet, annihilation may occur. The electron-positron annihilation may simultaneously generate two photons (e.g., 511-kiloelectron volt (keV) gamma photons) traveling in opposite directions along a line. The two photons may be detected by a pair of oppositely disposed detector units.

Each of the two photon generated by an electron-positron annihilation may strike the scintillator 212 to produce a burst of fluorescent light. The fluorescence may transmit from the scintillator 212 to the photodetector 214. The fluorescence may be converted to an electrical signal (e.g., an electrical pulse) by the photodetector 214. The electrical signal may be transmitted to other components of the PET system 100, such as the processing device 140.

In some embodiments, the detector unit 210 may further include a light guide (not shown in FIG. 2) configured to provide a light path to the photodetector 214. In some embodiments, a front-end circuit board (not shown in FIG. 2) may be coupled to the photodetector 214 to process electrical signals and/or transmit electrical signals to other components (e.g., the processing device 140) of the PET system 100.

The network 120 may facilitate exchange of information and/or data. In some embodiments, one or more components in the PET system 100 (e.g., the PET scanner 110, the terminal 130, the processing device 140, or the storage device 150) may send information and/or data to other component(s) in the PET system 100 via the network 120. For example, the processing device 140 may obtain electrical signals from the PET scanner 110 via the network 120. As another example, the processing device 140 may obtain user instructions from the terminal 130 via the network 120. In some embodiments, the network 120 may be any type of wired or wireless network, or combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In some embodiments, the network 120 may include one or more network access points. For example, the network 120 may include wired or wireless network access points such as base stations and/or internet exchange points through which one or more components of the PET system 100 may be connected to the network 120 to exchange data and/or information.

The terminal 130 may include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. The terminal 130 may remotely operate the PET scanner 110. In some embodiments, the terminal 130 may operate the PET scanner 110 via a wireless connection. In some embodiments, the terminal 130 may receive information and/or instructions inputted by a user, and transmit the received information and/or instructions to the PET scanner 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information obtained from the PET scanner 110, the terminal 130, or the storage device 150. For example, the processing device 140 may process electrical signals obtained from the PET scanner 110 and reconstruct an image based on the obtained electrical signals. As another example, the processing device 140 may determine a coincidence time window for an LOR. In some embodiments, the processing device 140 may be a single server, or a server group. The server group may be centralized, or distributed. In some embodiments, the processing device 140 may be local or remote. For example, the processing device 140 may access information and/or data stored in the PET scanner 110, the terminal 130, and/or the storage device 150 via the network 120. As another example, the processing device 140 may be directly connected to the PET scanner 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 300 having one or more components illustrated in FIG. 3 in the present disclosure.

The storage device 150 may store data and/or instructions. In some embodiments, the storage device 150 may store data obtained from the terminal 130 and/or the processing device 140. For example, the storage device 150 may store images generated by the processing device 140. In some embodiments, the storage device 150 may store data and/or instructions that the processing device 140 may execute or use to perform exemplary methods described in the present disclosure. For example, the storage device 150 may store instructions that the processing device 140 may execute or use to determine a coincidence time window. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components in the PET system 100 (e.g., the processing device 140, the terminal 130). One or more components of the PET system 100 may access the data or instructions stored in the storage device 150 via the network 120. In some embodiments, the storage device 150 may be directly connected to or communicate with one or more components in the PET system 100 (e.g., the processing device 140, the terminal 130). In some embodiments, the storage device 150 may be part of the processing device 140.

FIG. 3 is a schematic diagram illustrating exemplary hardware and/or software components of a computing device on which the processing device 140 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 310 may process data obtained from the PET scanner 110, the terminal 130, the storage device 150, or any other component of the PET system 100. Specifically, the processor 310 may process electrical signals obtained from the PET scanner 110. As another example, the processing device 140 may determine a coincidence time window for an LOR. In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be note that the computing device 300 in the present disclosure may also include multiple processors, thus operations and/or method steps that are performed by one processor as described in the present disclosure may also be jointly or separately performed by the multiple processors. For example, if in the present disclosure the processor of the computing device 300 executes both step A and step B, it should be understood that step A and step B may also be performed by two different processors jointly or separately in the computing device 300 (e.g., a first processor executes step A and a second processor executes step B, or the first and second processors jointly execute steps A and B).

The storage 320 may store data/information obtained from the PET scanner 110, the terminal 130, the storage device 150, or any other component of the PET system 100. In some embodiments, the storage 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 140 for determining a coincidence time window for an LOR.

The I/O 330 may input or output signals, data, or information. In some embodiments, the I/O 330 may enable a user interaction with the processing device 140. For example, the processing device may display an image through the I/O 330. In some embodiments, the I/O 330 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected to a network (e.g., the network 120) to facilitate data communications. The communication port 340 may establish connections between the processing device 140 and the PET scanner 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
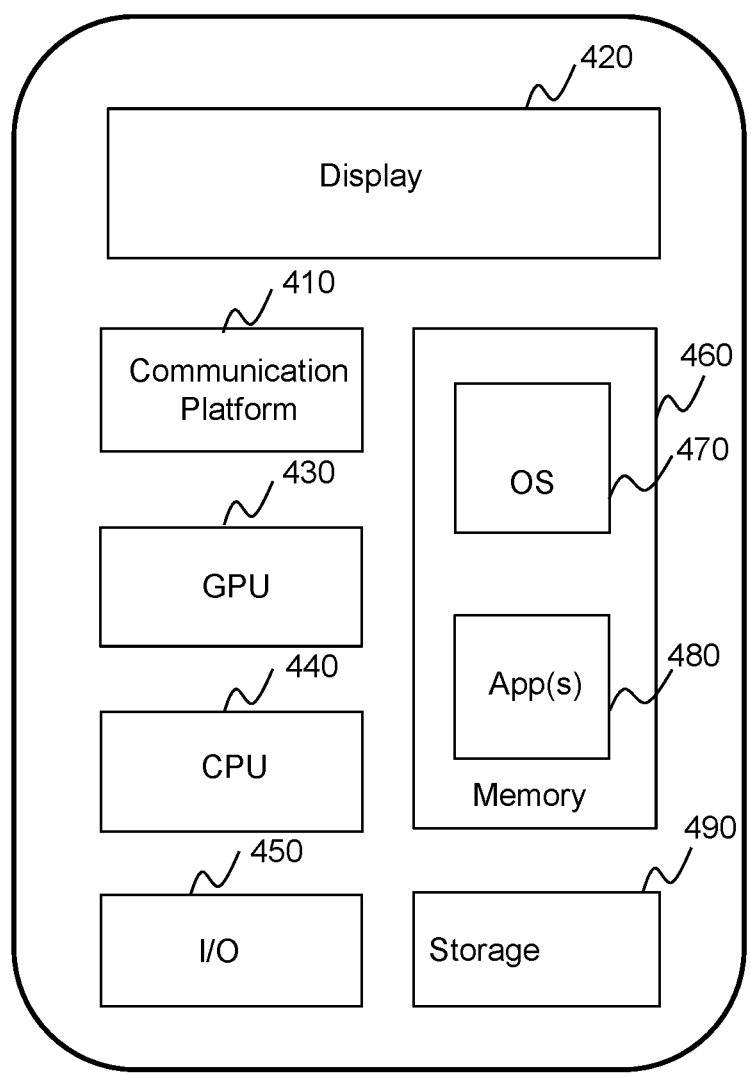
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device on which the terminal 130 may be implemented according to some embodiments of the present disclosure. As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the PET system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 5:
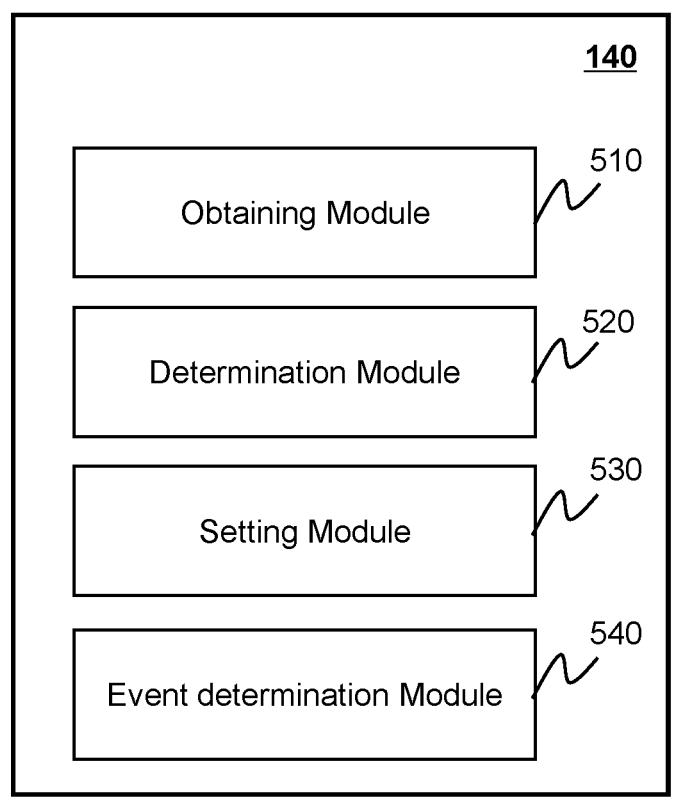
FIG. 5 is a block diagram illustrating an exemplary processing device according to some embodiments of the present disclosure.

FIG. 5 is a block diagram illustrating an exemplary processing device according to some embodiments of the present disclosure. The processing device 140 may include an obtaining module 510, a determination module 520, and a setting module 530. In some embodiments, the processing device 140 may further include an event determination module 540.

The obtaining module 510 may be configured to obtain first photon information of a first photon (e.g., gamma photon) that is emitted from an annihilation event occurred in an object and detected by a first detector unit of a PET detector (e.g., the detector 118 illustrated in FIG. 1 and/or FIG. 2).

In some embodiments, the first photon information may include a first incident angle at which the first photon reaches an incident surface of the first detector unit, a first detection time when the first detector unit detects the first photon, a first incident position at which the first photon reaches the incident surface of the first detector unit, energy of the first photon, the time of flight (TOF) of the first photon, or the like, or any combination thereof. The time for a photon to travel from its origin to a point where it is detected may be referred to as the time of flight (TOF) of the photon.

In some embodiments, the incident angle of a photon may refer to an angle between the incident direction and a line, e.g., a normal of the incident surface of the detector unit where the photon reaches a point of incidence (e.g., the incident position of the photon on the incident surface). Alternatively, the incident angle of a photon may refer to an angle between the incident direction and a surface, e.g., the incident surface of the detector unit.

In some embodiments, when the first detector unit detects the first photon, the first photon information may be recorded. The first photon information may be stored in the storage device 150 and/or may be transmitted to the processing device 140.

The determination module 520 may be configured to determine target LOR information of a target LOR related to the first photon based on the first photon information.

In some embodiments, the target LOR information may include first location information of the first detector unit, second location information of the second detector unit, a first length of the target LOR, the first incident angle, or the like, or any combination thereof.

In some embodiments, the location information of a detector unit may be represented using two-dimensional (2D) coordinates or three-dimensional (3D) coordinates. In some embodiments, the location information of a detector unit may be represented using Cartesian coordinates or polar coordinates.

The setting module 530 may be configured to determine a coincidence time window for the target LOR based on the target LOR information.

In some embodiments, when the first detector unit detects the first photon, the setting module 530 may set a coincidence time window for the first photon. The coincidence time window may be a concept of a time range. The first photon and a photon detected by the second detector unit within the coincidence time window may be determined as a coincidence event.

In some embodiments, the setting module 530 may determine a target window width based on the target LOR information of the target LOR. The setting module 530 may determine the coincidence time window for the first photon based on the target window width.

In some embodiments, the setting module 530 may determine the second length based on the target LOR information. In some embodiments, the setting module 530 may determine the second length based on the first incident angle. In some embodiments, the setting module 530 may determine the first length based on the target LOR information and determine the second length based on the first length, the diameter of the FOV (or a portion thereof that corresponds to the object or a portion of the object of interest), and the diameter of the bore of the detector 118. In some embodiments, the setting module 530 may determine the first length based on the first location information and the second location information. In some embodiments, the setting module 530 may determine the first length based on the first incident angle.

The event determination module 540 may be configured to obtain the second photon information of the second photon that is detected by the second detector unit of the detector 118 of the PET scanner 110. In some embodiments, the second photon information may include a second incident angle at which the second photon reaches an incident surface of the second detector unit, a second detection time when the second detector unit detects the second photon, a second incident position at which the second photon reaches the incident surface of the second detector unit, energy of the first photon, or any combination thereof.

The event determination module 540 may be also configured to determine whether the detection of the first photon and the detection of the second photon have occurred within the coincidence time window based on the first photon information and the second photon information.

In some embodiments, the event determination module 540 may determine a difference between the first detection time and the second detection time. The event determination module 540 may determine whether the difference is within the coincidence time window. In response to determining that the difference is within the coincidence time window, the event determination module 540 may determine that the detection of the first photon and the detection of the second photon occur within the coincidence time window. In response to determining that the difference is out of the coincidence time window, the event determination module 540 may determine that the detection of the first photon and the detection of the second photon do not occur within the coincidence time window.

In response to determining that the detection of the first photon and the detection of the second photon occur within the coincidence time window, the event determination module 540 may be also configured to determine that the first photon and the second photon are a coincidence event.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided to two or more units. For example, the obtaining module 510 may be divided into two units. The first unit may be configured to obtain the first photon information. The second unit may be configured to obtain the mapping relation.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of in the processing device 140. As another example, each of components of the processing device 140 may include a storage apparatus. Additionally or alternatively, the components of the processing device 140 may share a common storage apparatus.

Figure 6:
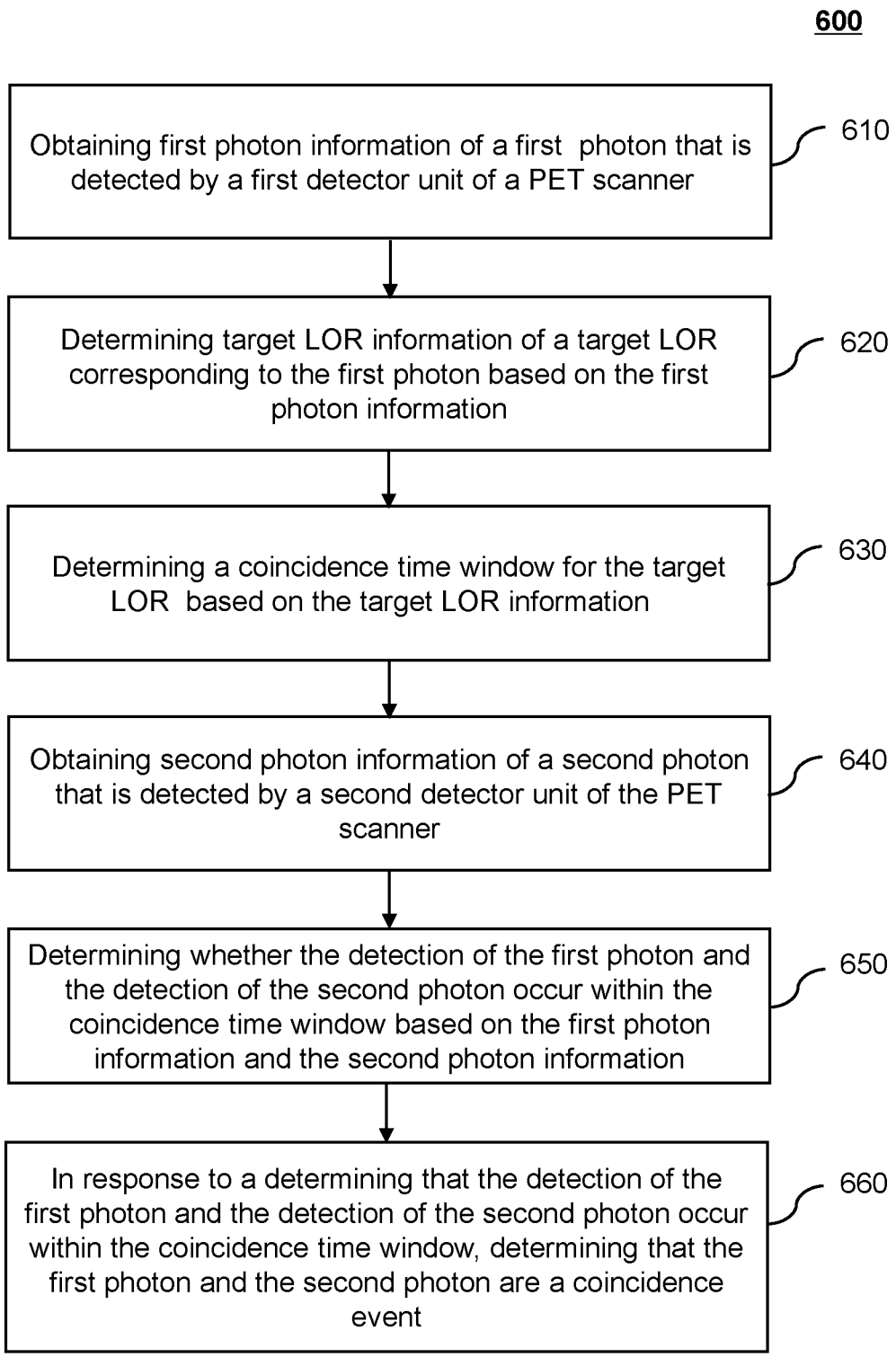
FIG. 6 is a flowchart illustrating an exemplary process for determining an annihilation event according to some embodiments of the present disclosure.

FIG. 6 is a flowchart illustrating an exemplary process for determining an annihilation event according to some embodiments of the present disclosure. The process 600 may be implemented in the PET system 100 illustrated in FIG. 1. For example, the process 600 may be stored in the storage device 150 and/or the storage 320 in the form of instructions (e.g., an application), and invoked and/or executed by the processing device 140 (e.g., the processor 310 illustrated in FIG. 3, or one or more modules in the processing device 140 illustrated in FIG. 5). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In some embodiments, the processing device 140 (e.g., the obtaining module 510) may obtain photon information of photons that are detected by detector units of a detector of a PET scanner (e.g., the detector 118 of the PET scanner 110 illustrated in FIG. 1 and/or FIG. 2). The photons may be emitted from an object. The processing device 140 (e.g., the determination module 520) may obtain, based on the photon information, more than one coincidence window width. Each of the more than one coincidence window width corresponds to at least one of target lines of response (LORs) of the photons. The processing device 140 (e.g., the event determination module 540) may determine coincidence events of the photons based on the photon information and the more than one coincidence window width. The processing device 140 may generate an image of the object based on the determined coincidence events of the photons.

For brevity, the process 600 for determining whether two of the photons are a coincidence event may be described as an example. The process for determining coincidence events related to the rest of the photons may be similar to the process 600.

In 610, the processing device 140 (e.g., the obtaining module 510) may obtain first photon information of a first photon (e.g., gamma photon) that is emitted from an annihilation event occurred in an object and detected by a first detector unit of a PET detector (e.g., the detector 118 illustrated in FIG. 1 and/or FIG. 2).

In some embodiments, the first photon information may include a first incident angle at which the first photon reaches an incident surface of the first detector unit, a first detection time when the first detector unit detects the first photon, a first incident position at which the first photon reaches the incident surface of the first detector unit, energy of the first photon, the time of flight (TOF) of the first photon, or the like, or any combination thereof. The time for a photon to travel from its origin to a point where it is detected may be referred to as the time of flight (TOF) of the photon.

In some embodiments, the incident angle of a photon may refer to an angle between the incident direction and a line, e.g., a normal of the incident surface of the detector unit where the photon reaches a point of incidence (e.g., the incident position of the photon on the incident surface). Alternatively, the incident angle of a photon may refer to an angle between the incident direction and a surface, e.g., the incident surface of the detector unit.

In some embodiments, when the first detector unit detects the first photon, the first photon information may be recorded. The first photon information may be stored in the storage device 150 and/or may be transmitted to the processing device 140.

In 620, the processing device 140 (e.g., the determination module 520) may determine target LOR information of a target LOR related to the first photon based on the first photon information.

Two photons emitted from a same annihilation event occurred in the object may penetrate the object along opposite directions. The two photons may impinge on and be detected by two detector units, respectively. In some embodiments, a positron-electron annihilation may be assumed to take place at a point on a straight line linking two detector units that detect the two photons generated in the positron-electron annihilation. The two photons may travel along the straight line towards opposite directions. The straight line may be referred to as a line of response (LOR). A positron-electron annihilation may correspond to an LOR. In some embodiments, the processing device 140 may determine a second detector unit based on the first incident angle. For example, the processing device 140 may determine the second detector unit along the opposite direction of the first incident angle. The straight line connecting the first detector unit and the second detector unit may refer to the target LOR related to the first photon. In some embodiments, the first and the second detector units may be located in the same detector ring or different detector rings of the detector 118.

In some embodiments, the target LOR information may include first location information of the first detector unit, second location information of the second detector unit, a first length of the target LOR, the first incident angle, or the like, or any combination thereof.

In some embodiments, the location information of a detector unit may be represented using two-dimensional (2D) coordinates or three-dimensional (3D) coordinates. In some embodiments, the location information of a detector unit may be represented using Cartesian coordinates or polar coordinates.

In 630, the processing device 140 (e.g., the setting module 530) may determine a coincidence time window for the target LOR based on the target LOR information.

In some embodiments, when the first detector unit detects the first photon, the processing device 140 may set a coincidence time window for the target LOR of the first photon. The coincidence time window may be a concept of a time range. The first photon and a photon detected by the second detector unit within the coincidence time window may be determined as a coincidence event.

In some embodiments, the processing device 140 may determine a target window width based on the target LOR information of the target LOR. The processing device 140 may determine the coincidence time window for the first photon based on the target window width.

Figure 7:
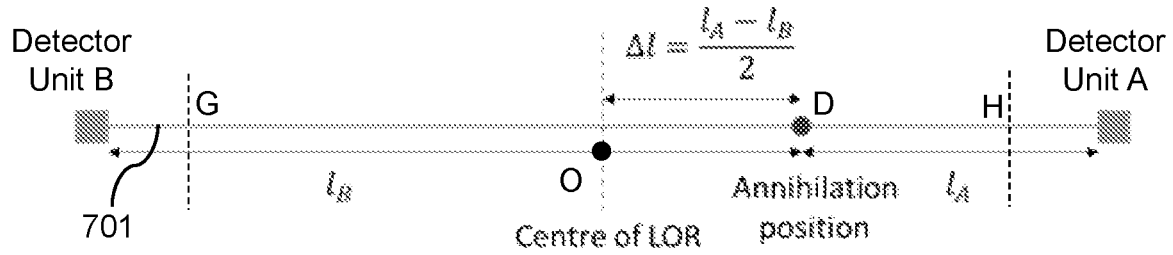
FIG. 7 is a schematic diagram illustrating an exemplary LOR according to some embodiments of the present disclosure.

FIG. 7 is a schematic diagram illustrating an exemplary LOR according to some embodiments of the present disclosure. As shown in FIG. 7, line 701 may be an LOR connecting detector unit A and detector unit B of the detector 118. If an annihilation event occurs at the center O of the LOR 701, the TOF ($T_A$) of the photon detected by the detector unit A may be equal to the TOF ($T_B$) of the photon detected by the detector unit B. If an annihilation event occurs at location D, a distance $\Delta l$ from the center O of the LOR 701, a time difference between $T_A$ and $T_B$ may be $$\Delta T = T_A - T_B = \frac{l_A - l_B}{c} = \frac{2\Delta l}{c},$$

where c refers to the speed of light; $l_A$ refers to a distance between the detector unit A and location D; $l_B$ refers to a distance between the detector unit B and location D;

$$l_A = T_A \times c, \; l_B = T_B \times c, \text{ and } \Delta l = \frac{l_A - l_B}{2}.$$

If L refers to a length of a segment GH of the LOR 701 in the FOV of the PET scanner 110, the TOF difference $\Delta T$ may take any value from $-L/c$ to $+L/c$, depending on the location of the annihilation event. Because a source or location of an annihilation event is unknown, the coincidence time window may be set to be large enough to accept all true coincidence events occurring within the FOV, so the window width may be set equal to or greater than 2 L/c.

In some embodiments, according to the above principle, the processing device 140 may determine the target window width based on a second length of a segment of the target LOR in the FOV of the PET scanner 110. In some embodiments, if it is known which portion of the FOV of the PET scanner 110 is occupied by the object, or a portion thereof that is of interest (e.g., the torso of a patient, the head of the patient), the processing device 140 may determine the target window width based on a second length of a segment of the target LOR in the portion of the FOV or the location and/or dimension of the object (or a portion thereof that is of interest) in the PET scanner 110. For convenience, the object, or a portion thereof that is of interest, may be mimicked or approximated using a shape. For instance, if the object is a patient, or a portion thereof that is of interest, may be mimicked using a cylinder, and the processing device 140 may determine the target window width based on a second length of a segment of the target LOR in the portion of the FOV that corresponds to the cylinder, or the location and/or dimension of the cylinder, in the PET scanner 110.

In some embodiments, the processing device 140 may determine the second length based on the target LOR information. In some embodiments, the processing device 140 may determine the second length based on the first incident angle. In some embodiments, the processing device 140 may determine the first length based on the target LOR information and determine the second length based on the first length, the diameter of the FOV (or a portion thereof that corresponds to the object or a portion of the object of interest), and the diameter of the bore of the detector 118. In some embodiments, the processing device 140 may determine the first length based on the first location information and the second location information. In some embodiments, the processing device 140 may determine the first length based on the first incident angle.

Figure 8:
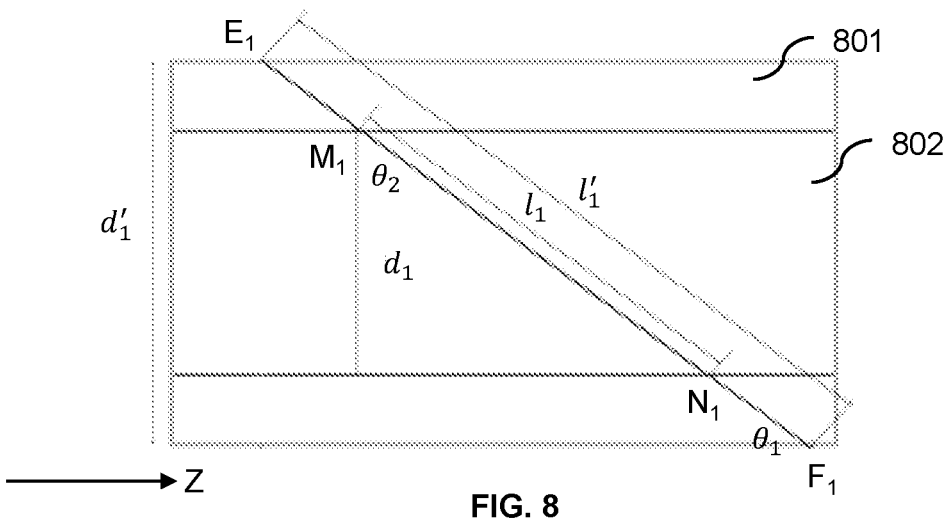
FIG. 8 is a schematic diagram illustrating an exemplary cross section of a PET detector parallel to a Z direction of the PET detector and an exemplary target LOR connecting two detector units that are in different detector rings of the PET detector according to some embodiments of the present disclosure.

Merely by way of example, FIG. 8 is a schematic diagram illustrating an exemplary longitudinal section of the detector 118 perpendicular to the X-Y plane and an exemplary target LOR connecting two detector units that are in different detector rings according to some embodiments of the present disclosure. The three-dimensional coordinate system illustrated in FIG. 2 applies here. Accordingly, the Z direction in FIG. 8 corresponds to the Z direction in FIG. 2. As shown in FIG. 8, space 801 refers to the bore of the detector 118, and space 802 refers to the FOV of the PET scanner 110. Line $E_1F_1$ refers to the target LOR, and $M_1N_1$ refers to a segment of the target LOR in the FOV 802. Length $d_1'$ refers to the diameter of the bore 801. Length $d_1$ refers to the diameter of the FOV 802. Length $l_1'$ refers to the first length of the target LOR $E_1F_1$. Length $l_1$ refers to the second length of the segment $M_1N_1$ of the target LOR in the FOV 802.

In some embodiments, if the first incident angle is an angle between the incident surface of the first detector unit and the first incident direction (e.g., $\theta_1$ shown in FIG. 8), the processing device 140 may determine the second length $l_1$ based on Equation (1) below:

$$l_1 = d_1/\sin\theta_1. \tag{1}$$

In some embodiments, if the first incident angle is an angle between the normal perpendicular to the incident surface of the first detector unit and the first incident direction (e.g., $\theta_2$ shown in FIG. 8), the processing device 140 may determine the second length $l_1$ based on Equation (2) below:

$$l_1 = d_1/\cos\theta_2. \tag{2}$$

In some embodiments, the first location information and the second location information may be represented as $(X_i, Y_i, Z_i)$ and $(X_j, Y_j, Z_j)$, respectively. The processing device 140 may determine the first length $l_1'$ based on Equation (3) below:

$$l_1' = \sqrt{(X_i-X_j)^2+(Y_i-Y_j)^2+(Z_i-Z_j)^2}. \tag{3}$$

In some embodiments, if the first incident angle is an angle between the incident surface of the first detector unit and the first incident direction (e.g., $\theta_1$ shown in FIG. 8), the processing device 140 may determine the first length $l_1'$ based on Equation (4) below:

$$l_1' = d_1'/\sin\theta_1. \tag{4}$$

In some embodiments, if the first incident angle is an angle between the normal perpendicular to the incident surface of the first detector unit and the first incident direction (e.g., represented as $\theta_2$), the processing device 140 may determine the first length $l_1'$ based on Equation (5) below:

$$l_1' = d_1'/\cos\theta_2. \tag{5}$$

In some embodiments, the processing device 140 may determine the second length based on the first length, the diameter of the FOV, and the diameter of the bore of the detector 118 using Equation (6) below:

$$l_1 = l_1' \times \frac{d_1}{d_1'}. \tag{6}$$

Figure 9:
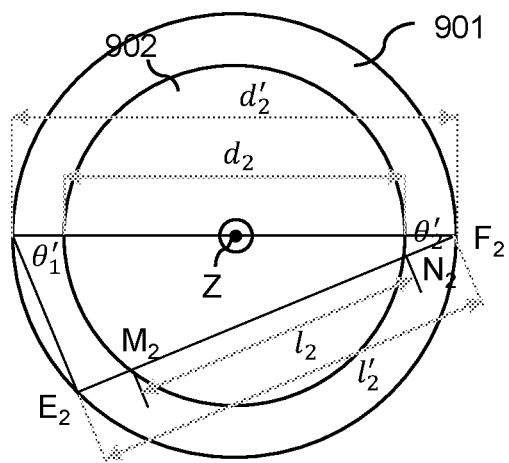
FIG. 9 is a schematic diagram illustrating an exemplary cross section of a PET detector perpendicular to a Z direction of the PET detector and an exemplary target LOR connecting two detector units that are in the same detector ring of the PET detector according to some embodiments of the present disclosure.

Merely by way of example, FIG. 9 is a schematic diagram illustrating an exemplary cross section of the detector 118 perpendicular to the Z direction and an exemplary target LOR connecting two detector units that are in the same detector ring according to some embodiments of the present disclosure. The three-dimensional coordinate system illustrated in FIG. 2 applies here. Accordingly, the Z direction in FIG. 9 corresponds to the Z direction in FIG. 2 and FIG. 8. As shown in FIG. 9, space 901 refers to the bore of the detector 118, and space 902 refers to the FOV of the PET scanner 110. Line $E_2F_2$ refers to the target LOR, and $M_2N_2$ refers to a segment of the target LOR $E_2F_2$ in the FOV 902. Length $d_2'$ refers to the diameter of the bore 901 of the detector 118. Length $d_2$ refers to the diameter of the FOV 902. Length $l_2'$ refers to the first length of the target LOR $E_2F_2$. Length $l_2$ refers to the second length of the segment $M_2N_2$ of the target LOR in the FOV 902.

In some embodiments, if the first incident angle is an angle between the incident surface of the first detector unit and the first incident direction (e.g., 0 shown in FIG. 9), the processing device 140 may determine the second length $l_2$ based on Equation (7) below:

$$l_2 = d_2^2 - [(d_2')^2 \times \cos \theta_1']^2. \tag{7}$$

In some embodiments, if the first incident angle is an angle between the normal perpendicular to the incident surface of the first detector unit and the first incident direction (e.g., $\theta_2'$ shown in FIG. 9), the processing device 140 may determine the second length $l_2$ based on Equation (8) below:

$$l_2 = d_2^2 - [(d_2')^2 \times \sin \theta_2']^2. \tag{8}$$

In some embodiments, the first location information and the second location information may be represented as $(X_i, Y_i)$ and $(X_j, Y_j)$, respectively. The processing device 140 may determine the first length $l_2'$ based on Equation (9) below:

$$l_2' = \sqrt{(X_i - X_j)^2 + (Y_i - Y_j)^2}. \tag{9}$$

In some embodiments, the first location information and the second location information may be represented as $(X_i, Y_i, Z_i)$ and $(X_j, Y_j, Z_j)$, respectively. The processing device 140 may determine the first length $l_2'$ based on Equation (3).

In some embodiments, if the first incident angle is an angle between the incident surface of the first detector unit and the first incident direction (e.g., $\theta_1'$ shown in FIG. 9), the processing device 140 may determine the first length $l_2'$ based on Equation (10) below:

$$l_2' = d_2' \times \sin \theta_1'. \tag{10}$$

In some embodiments, if the first incident angle is an angle between the normal perpendicular to the incident surface of the first detector unit and the first incident direction (e.g., represented as $\theta_2'$), the processing device 140 may determine the first length $l_2'$ based on Equation (11) below:

$$l_2' = d_2' \times \cos \theta_2'. \tag{11}$$

In some embodiments, the processing device 140 may determine the second length $l_2$ based on the first length, the diameter of the FOV, and the diameter of the bore of the detector 118 using Equation (12) below:

$$l_2 = \sqrt{d_2^2 - (d_2')^2 + (l_2')^2}. \tag{12}$$

In some embodiments, the processing device 140 may determine the target window width based on the second length using Equation (13) below:

$$CTW = \frac{2l}{c}, \tag{13}$$

wherein CTW refers to the target window width; l refers to the second length (e.g., $l_1$ or $l_2$); and c refers to the speed of light.

In some embodiments, the processing device 140 may determine the target window width based further on a coincidence temporal resolution of the PET scanner 110. For example, the processing device 140 may determine the target window width based on the Equation (14) below:

$$CTW = \frac{2l}{c} + n\sigma, \tag{14}$$

wherein σ refers to the coincidence temporal resolution of the PET scanner 110; and n refers to an empirical parameter that is configured to adjust the target window width.

FIGS. 8 and 9, as well as Equations (1)-(14), are provided with reference to the determination of the second length based on the diameter of the FOV for illustration purposes and not intended to be limiting. If the second length is determined based on the diameter of a portion thereof that corresponds to the object or a portion of the object of interest, length $d_1$ or $d_2$ in Equations (1)-(14) refers to a dimension of the portion of the FOV.

In some embodiments, after detecting the first photon, the processing device 140 may determine the target window width based on the target LOR information using, for example, at least one of Equations (1)-(14) above.

In some embodiments, the processing device 140 may obtain a mapping relation between each LOR of the detector 118 and the corresponding window width. The mapping relation may include a relation between one or more parameters of an LOR and the corresponding window width. Exemplary parameters of an LOR may include the length of the LOR, the location information of the pair of detector units connected by the LOR, the incident angle corresponding to the LOR, etc. In some embodiments, the processing device 140 may determine the target window width by consulting the mapping relation based on the target LOR information. For example, the processing device 140 may determine the target window width by consulting the mapping relation based on the first and the second location information. As another example, the processing device 140 may determine the target window width by consulting the mapping relation based on the first incident angle. As further another example, the processing device 140 may determine the target window width by consulting the mapping relation based on the first length of the target LOR.

In some embodiments, the mapping relation may be determined in advance and may be stored in a storage device (e.g., the storage device 150, the storage 320, etc.) of the PET system 100. The processing device 140 may obtain the mapping relation from the storage device. In some embodiments, the processing device 140 may obtain the mapping relation from other system communicating with the PET system 100. In some embodiments, the mapping relation may be determined by the processing device 140 or another system. Details related to determining the mapping relation may be found elsewhere in the present disclosure (e.g., description in connection with FIG. 10).

In some embodiments, the processing device 140 may set the coincidence time window for the first photon based on the target window width. For example, the target window width may be determined as $$\frac{2l}{c}.$$

The processing device 140 may set the coincident time window as $$\left[-\frac{l}{c}, \frac{l}{c}\right].$$

In 640, the processing device 140 (e.g., the event determination module 540) may obtain second photon information of a second photon that is detected by the second detector unit of the detector 118 of the PET scanner 110. In some embodiments, the second photon information may include a second incident angle at which the second photon reaches an incident surface of the second detector unit, a second detection time when the second detector unit detects the second photon, a second incident position at which the second photon reaches the incident surface of the second detector unit, energy of the first photon, or any combination thereof.

In 650, the processing device 140 (e.g., the event determination module 540) may determine whether the detection of the first photon and the detection of the second photon have occurred within the coincidence time window based on the first photon information and the second photon information.

In some embodiments, the processing device 140 may determine a difference between the first detection time and the second detection time. The processing device 140 may determine whether the difference is within the coincidence time window. In response to determining that the difference is within the coincidence time window, the processing device 140 may determine that the detection of the first photon and the detection of the second photon occur within the coincidence time window. In response to determining that the difference is out of the coincidence time window, the processing device 140 may determine that the detection of the first photon and the detection of the second photon do not occur within the coincidence time window.

In 660, in response to determining that the detection of the first photon and the detection of the second photon occur within the coincidence time window, the processing device 140 (e.g., the event determination module 540) may determine that the first photon and the second photon are a coincidence event.

In some embodiments, when a first detector unit of the detector 118 detects a first photon, LORs that the first photon possibly originates from may be determined based on the incident angle of the first photon. The LORs may connect the first detector unit and other detector units. For each of the LORs, a coincidence time window may be set based on operations 620-630. According to operations 640-660, the first photon and photons detected by the other detector units within the corresponding coincidence time windows may be determined as coincidence events. The determined coincidence events may include true coincidence events and random coincidence events. Compared to a uniform coincidence time window for all LORs, such LOR-dependent coincidence time windows may be used to identify, from a large amount of single events, candidate single events more precisely, and accordingly reduce erroneously determined LORs and/or reduce the amount of single events to be processed in the coincident event determination and the random coincidence events, which in turn may improve the accuracy and/or efficiency in determining coincidence events and the image quality of the PET system.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 10:
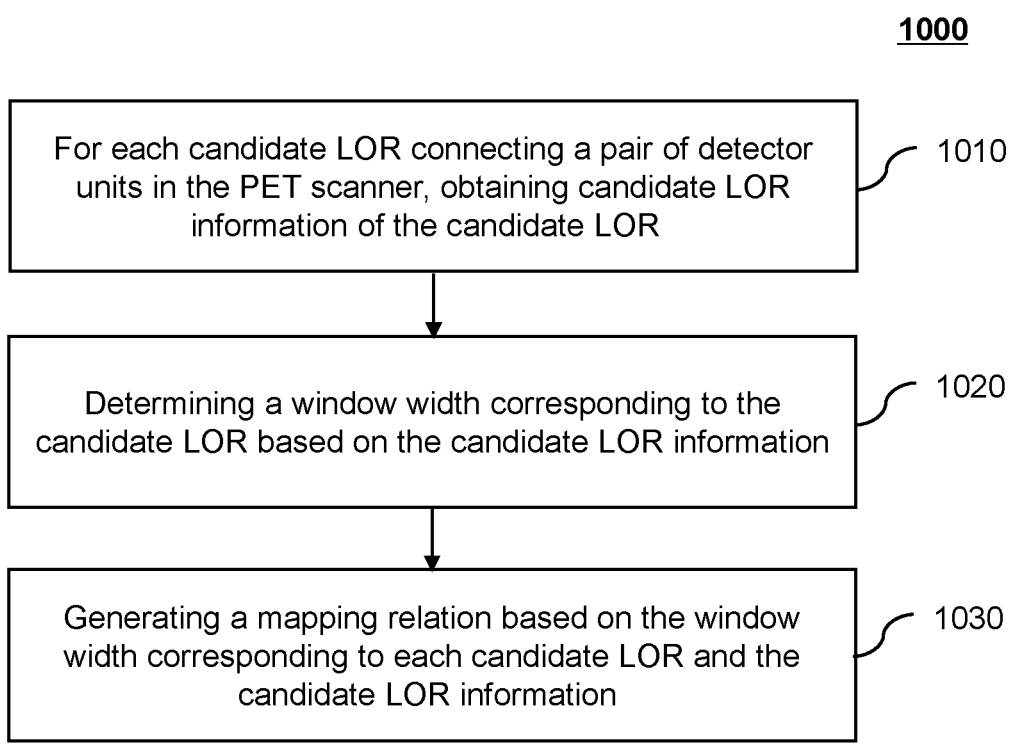
FIG. 10 is a flowchart illustrating an exemplary process for determining a mapping relation according to some embodiments of the present disclosure.

FIG. 10 is a flowchart illustrating an exemplary process for determining a mapping relation according to some embodiments of the present disclosure. The process 1000 may be implemented in the PET system 100 illustrated in FIG. 1. For example, the process 1000 may be stored in the storage device 150 and/or the storage 320 in the form of instructions (e.g., an application), and invoked and/or executed by the processing device 140 (e.g., the processor 310 illustrated in FIG. 3, or one or more modules in the processing device 140 illustrated in FIG. 5). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1010, the processing device 140 (e.g., the obtaining module 510) may obtain, for each candidate LOR connecting a pair of detector units in the detector 118 of the PET scanner 110, candidate LOR information of the candidate LOR. In some embodiments, the candidate LOR information may include the location information of the pair of detector units connected by the candidate LOR, a length of the candidate LOR, an incident angle corresponding to the candidate LOR, or the like, or any combination thereof.

In 1020, the processing device 140 (e.g., the obtaining module 510) may determine a window width corresponding to the candidate LOR based on the candidate LOR information. In some embodiments, the processing device 140 may determine the window width corresponding to the candidate LOR based on the candidate LOR information using, for example, at least one of Equations (1)-(14) above.

In 1030, the processing device 140 (e.g., the obtaining module 510) may generate a mapping relation based on the window width corresponding to each candidate LOR and the candidate LOR information. In some embodiments, the mapping relation may include a relation between the window width corresponding to each candidate LOR and at least one of the location information of the pair of detector units connected by the candidate LOR, the length of the candidate LOR, and the incident angle corresponding to the candidate LOR.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the process 1000 for determining the mapping relation may be performed by another system.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for positron emission tomography (PET) imaging, comprising:
   at least one storage device storing a set of instructions; and
   at least one processor in communication with the at least one storage device, wherein when the at least one processor executes the set of instructions, the system is caused to perform operations including:
   obtaining photon information of photons that are emitted from an object and detected by detector units of a detector of a PET scanner;
   determining at least one target line of response (LOR) corresponding to the photons based on the photon information;
   for each of the at least one target LOR, obtaining a coincidence window width value that is determined based on a first length of the target LOR linking two of the detector units of the detector or a second length of a segment of the target LOR in a field of view (FOV) of the PET scanner, wherein the segment of the target LOR in the FOV refers to a portion of the target LOR between two intersections of the target LOR with a periphery of the FOV; and
   determining coincidence events of the photons based on the coincidence window width value of the at least one target LOR.

2. The system of claim 1, wherein for each of the at least one target LOR, obtaining the coincidence window width value includes:
   determining, based on the photon information, target LOR information of the at least one target LOR; and
   obtaining the coincidence window width value based on the target LOR information of the at least one target LOR.

3. The system of claim 2, wherein for each of the at least one target LOR, determining the coincidence window width value includes:
   obtaining a mapping relation between the coincidence window width value and the target LOR information of the at least one target LOR; and
   obtaining the coincidence window width value by consulting the mapping relation based on the target LOR information of the at least one target LOR.

4. The system of claim 3, wherein the mapping relation is provided by
   for each candidate LOR connecting two of the detector units of the detector in the PET scanner,
   obtaining candidate LOR information of the candidate LOR;
   determining a third length of a segment of the candidate LOR in the FOV of the PET scanner based on the candidate LOR information; and
   determining a candidate window width value corresponding to the candidate LOR based on the third length; and
   generating the mapping relation based on the candidate window width value corresponding to each candidate LOR and the candidate LOR information, the candidate LORs including the target LORs.

5. The system of claim 4, wherein the candidate LOR information of the candidate LOR includes at least one of a fourth length of the candidate LOR, an incident angle corresponding to the candidate LOR, and location information of the two of the detector units connected by the candidate LOR.

6. The system of claim 5, wherein the determining the third length of the segment of the candidate LOR in the FOV of the PET scanner based on the candidate LOR information includes:
   determining the third length based on the fourth length of the candidate LOR, a diameter of a bore of the PET scanner, and a diameter of the FOV.

7. The system of claim 5, wherein the determining the third length of the segment of the candidate LOR in the FOV of the PET scanner based on the candidate LOR information includes:
   determining the third length based on the incident angle corresponding to the candidate LOR.

8. The system of claim 2, wherein the second length of the segment of the target LOR in the FOV is determined based on the target LOR information of the target LOR.

9. The system of claim 1, wherein the coincidence window width value corresponding to the target LOR is determined based on the segment of the target LOR in the FOV and a speed of light.

10. The system of claim 1, wherein the coincidence window width value corresponding to the target LOR is determined based further on a coincidence temporal resolution of the PET scanner.

11. The system of claim 1, wherein the second length of the segment of the target LOR in the FOV is determined based on at least one of a diameter of the FOV or a diameter of a bore of the detector.

12. The system of claim 1, wherein the coincidence window width value is determined without prior reconstruction of one or more images obtained by scanning the object.

13. A method for positron emission tomography (PET) imaging implemented on a machine including one or more processors and one or more storage devices, comprising:
   obtaining photon information of photons that are emitted from an object and detected by detector units of a detector of a PET scanner;
   determining at least one target line of response (LOR) corresponding to the photons based on the photon information;
   for each of the at least one target LOR, obtaining a coincidence window width value that is determined based on a first length of the target LOR linking two of the detector units of the detector or a second length of a segment of the target LOR in a field of view (FOV) of the PET scanner, wherein the segment of the target LOR in the FOV refers to a portion of the target LOR between two intersections of the target LOR with a periphery of the FOV; and
   determining coincidence events of the photons based on the coincidence window width value of the at least one target LOR.

14. The method of claim 13, wherein for each of the at least one target LOR, obtaining the coincidence window width value includes:
   determining, based on the photon information, target LOR information of the at least one target LOR; and
   obtaining the coincidence window width value based on the target LOR information of the at least one target LOR.

15. The method of claim 14, wherein for each of the at least one target LOR, determining the coincidence window width value includes:
- obtaining a mapping relation between the coincidence window width value and the target LOR information of the at least one target LOR; and
- obtaining the coincidence window width value by consulting the mapping relation based on the target LOR information of the at least one target LOR.

16. The method of claim 15, wherein the mapping relation is provided by
- for each candidate LOR connecting two of the detector units of the detector in the PET scanner,
- obtaining candidate LOR information of the candidate LOR;
- determining a third length of a segment of the candidate LOR in the FOV of the PET scanner based on the candidate LOR information; and
- determining a candidate window width value corresponding to the candidate LOR based on the third length; and
- generating the mapping relation based on the candidate window width value corresponding to each candidate LOR and the candidate LOR information, the candidate LORs including the target LOR.

17. The method of claim 16, wherein the determining the third length of the segment of the candidate LOR in the FOV of the PET scanner based on the candidate LOR information includes:
- determining the third length based on a fourth length of the candidate LOR, a diameter of a bore of the PET scanner, and a diameter of the FOV.

18. The method of claim 16, wherein the determining the third length of the segment of the candidate LOR in the FOV of the PET scanner based on the candidate LOR information includes:
- determining the third length based on an incident angle corresponding to the candidate LOR.

19. The method of claim 13, wherein the coincidence window width value corresponding to the target LOR is determined based further on a coincidence temporal resolution of the PET scanner.

20. A non-transitory computer readable medium, comprising at least one set of instructions, wherein when executed by one or more processors of a computing device, the at least one set of instructions causes the computing device to perform a method, the method comprising:
- obtaining photon information of photons that are emitted from an object and detected by detector units of a detector of a PET scanner;
- determining at least one target line of response (LOR) corresponding to the photons based on the photon information;
- for each of the at least one target LOR, obtaining a coincidence window width value that is determined based on a first length of the target LOR linking two of the detector units of the detector or a second length of a segment of the target LOR in a field of view (FOV) of the PET scanner, wherein the segment of the target LOR in the FOV refers to a portion of the target LOR between two intersections of the target LOR with a periphery of the FOV; and
- determining coincidence events of the photons based on the coincidence window width value of the at least one target LOR.

* * * * *